US008771760B2

(12) United States Patent
Guy et al.

(10) Patent No.: US 8,771,760 B2
(45) Date of Patent: Jul. 8, 2014

(54) METHOD FOR THE TREATMENT OF CONSTIPATION

(75) Inventors: Geoffrey Guy, Glanvilles Wootton (GB); Philip Robson, Salisbury (GB)

(73) Assignee: GW Pharma Limited, Salisbury (GB)

( * ) Notice: Subject to any disclaimer, the term of this patent is extended or adjusted under 35 U.S.C. 154(b) by 416 days.

(21) Appl. No.: 13/093,911

(22) Filed: Apr. 26, 2011

(65) Prior Publication Data

US 2011/0230549 A1   Sep. 22, 2011

Related U.S. Application Data

(63) Continuation of application No. 11/115,983, filed on Apr. 27, 2005, now Pat. No. 7,968,594.

(51) Int. Cl.
*A61K 36/00* (2006.01)
*A61K 31/35* (2006.01)
*A61K 31/07* (2006.01)

(52) U.S. Cl.
USPC .......................... 424/725; 514/454; 514/725

(58) Field of Classification Search
USPC ................................ 424/725; 514/454, 725
See application file for complete search history.

(56) References Cited

U.S. PATENT DOCUMENTS

| 6,730,330 B2 | 5/2004 | Whittle et al. |
| 7,025,992 B2 | 4/2006 | Whittle et al. |
| 7,968,594 B2 | 6/2011 | Guy et al. |

FOREIGN PATENT DOCUMENTS

GB        2377633        1/2003

OTHER PUBLICATIONS

Hanuš et al., "Cannabinoid chemistry: an overview", Cannabinoids as Therapeutics, pp. 23-46 (2005).*

Coffman et al., Cannabinoid Profile and Elemental Uptake of *Cannabis sativa* L. as Influenced by Soil Characteristics, Agronomy Journal, vol. 67, No. 4, pp. 491-497 (1975).*
[No author listed] "Opiate." Answers.com Reference Answers. Accessed on Jul. 20, 2007 at www.answer.com/topic/opiate?cat=health. 7 pages.
[No author listed] GW announces positive preliminary results with its cannabis-based-medicine (Sativex®) in phase III cancer pain trial. GW Pharma News Release. Jan. 19, 2005.
[No author listed] Quality improvement guidelines for the treatment of acute pain and cancer pain. American Pain Society Quality of Care Committee. JAMA. Dec. 20, 1995;274(23):1874-80.
Formukong et al., Analgesic and antiinflammatory activity of constituents of *Cannabis sativa* L. Inflammation. Aug. 1988;12(4):361-71.
Holdcroft et al., Clinical trial experience with cannabinoids. Pharm Sci. Nov. 1997;3(11):546-50.
Holdcroft et al., Pain relief with oral cannabinoids in familial Mediterranean fever. Anaesthesia. May 1997;52(5):483-6.
Noyes et al., The analgesic properties of delta-9-tetrahydrocannabinol and codeine. Clin Pharmacol Ther. Jul. 1975;18(1):84-9.
The United Kingdom Parliament, Select Committee on Science and Technology—Ninth Report. Nov. 4, 1998. http://www.parliament.the-stationery-office.co.uk/pa/ld199798/ldselect/ldsctech/151/15101.htm.
The United Kingdom Parliament, Select Committee on Science and Technology—Second Report. Mar. 14, 2001. http://www.publications.parliament.uk/pa/ld200001/ldselect/ldsctech/50/5001.htm.
[No Author Listed] Cannabinoid. Wikipedia, the free encyclopedia. Last accessed at http://en.wikipedia.org/wiki/Cannabinoid on Aug. 12, 2009.

* cited by examiner

*Primary Examiner* — Kevin E Weddington
(74) *Attorney, Agent, or Firm* — Wolf, Greenfield & Sacks, P.C.

(57)        ABSTRACT

The present invention relates to treatment of cancer related pain and constipation. Preferably the subject in need is administered a combination of the cannabinoids cannabidiol (CBD) and delta-9-tetrahydrocannabinol (THC). More preferably the cannabinoids are in a predefined ratio by weight of approximately 1:1 of CBD to THC.

1 Claim, 3 Drawing Sheets

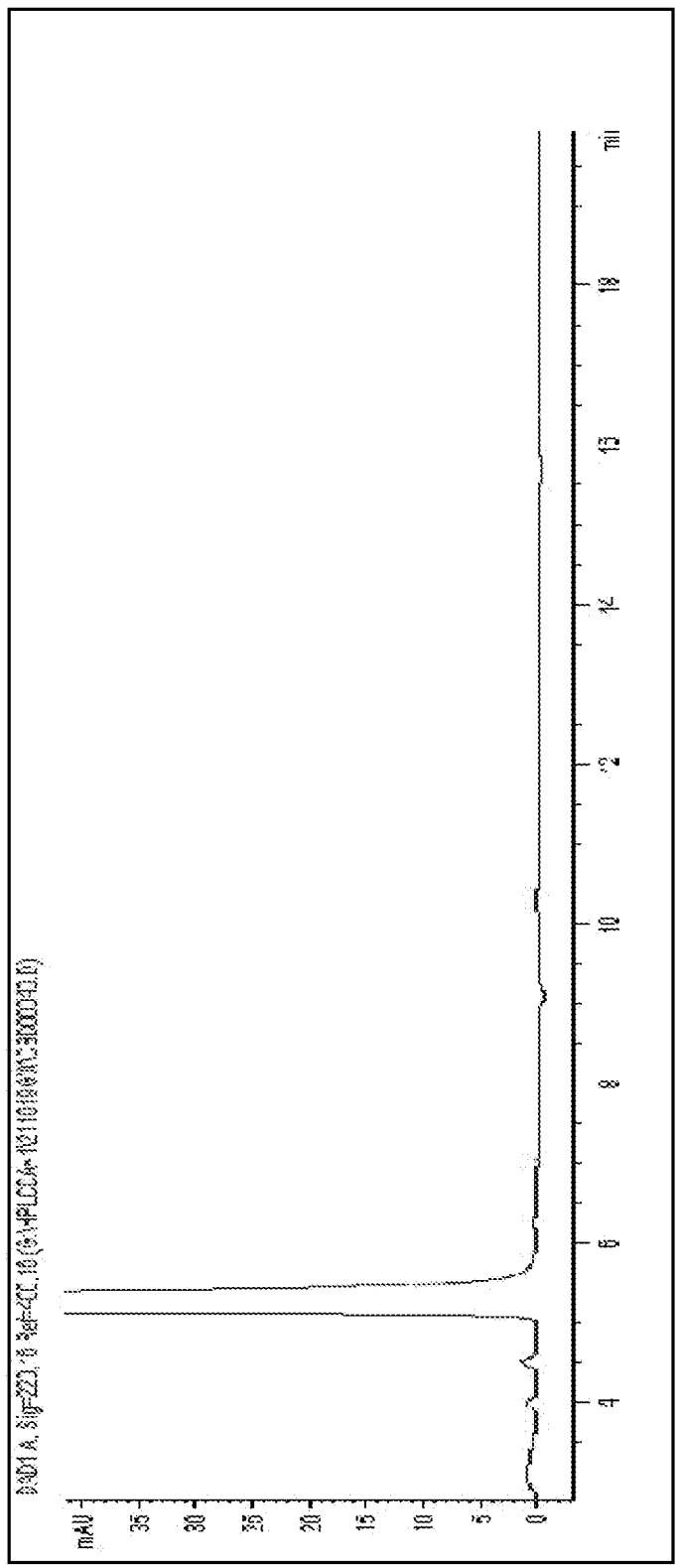
Figure 1. An HPLC chromatographic profile of a CBD-containing CBME

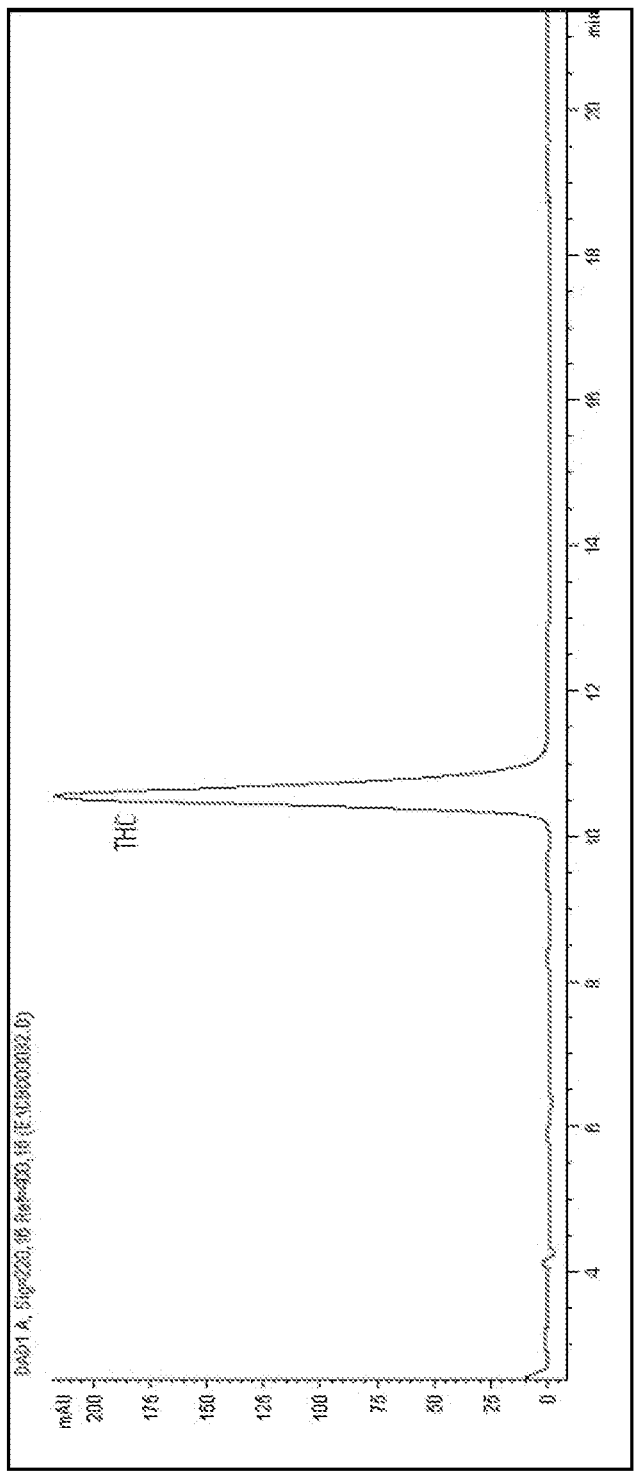
Figure 2. An HPLC chromatographic profile of a THC-containing CBME

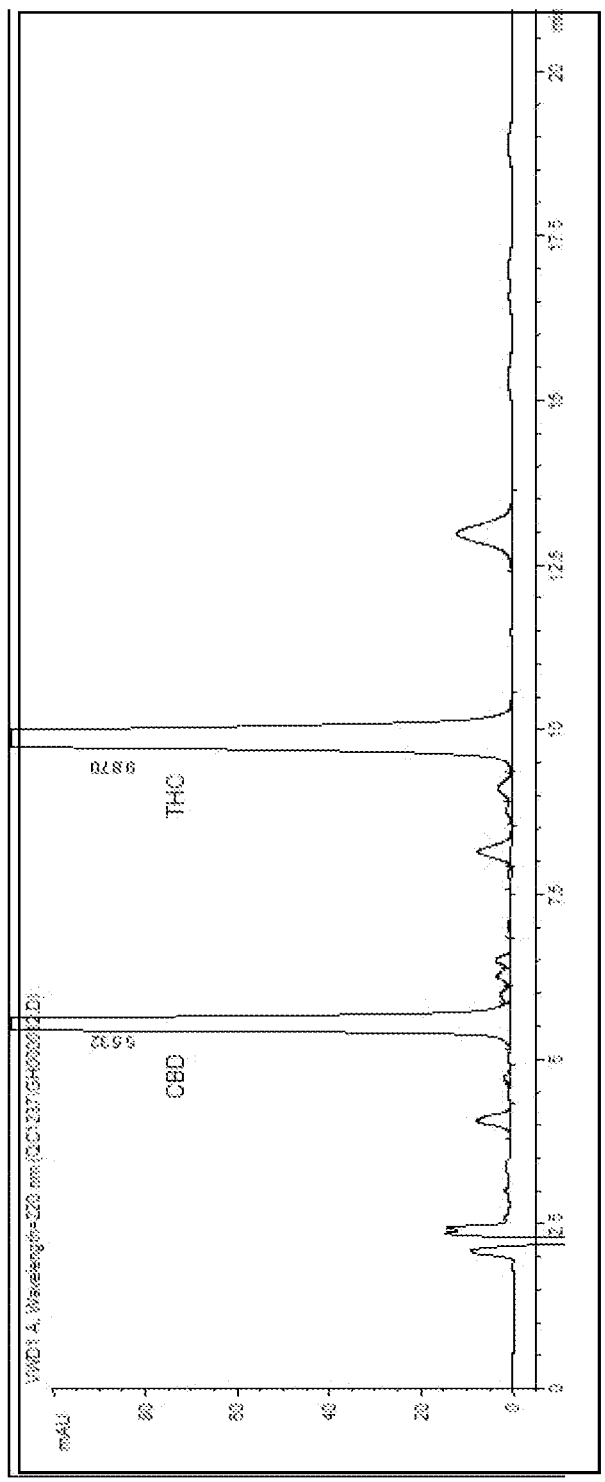

METHOD FOR THE TREATMENT OF CONSTIPATION

RELATED APPLICATIONS

This application is a continuation of U.S. patent application Ser. No. 11/115,983, filed Apr. 27, 2005, now allowed, which application is incorporated herein by reference.

FIELD OF THE INVENTION

The present invention relates to treatment of cancer related pain and constipation. Preferably the subject in need is administered a combination of the cannabinoids cannabidiol (CBD) and delta-9-tetrahydrocannabinol (THC). More preferably the cannabinoids are in a predefined ratio by weight of approximately 1:1 of CBD to THC.

BACKGROUND OF THE INVENTION

Pain, in particular chronic pain, can be a severely debilitating problem for many patients and it is often the case that the disease that is causing the pain itself becomes untreatable and the main focus of care is then altered to be palliative.

Even though the doctors and care providers best intentions are to provide optimum care for the patient, pain and symptom control can often not be as effective as hoped as the entire healthcare system has been designed to cure disease rather than alleviate pain and symptoms.

Effectively treating chronic pain poses a great challenge for doctors and health care providers as this type of pain often affects a patient's quality of life. A person's ability to carry out everyday tasks can be severely compromised due to chronic pain and as such the patient's personality can change.

For example when a patient is suffering from chronic pain caused by terminal cancer the only treatment option available is the relief of pain. Unfortunately up to 40% of cancer sufferers have unmet needs in pain suppression at the present time.

The caregiver's requirements are to provide the patient with a sufficient dose of medication to allow them to be freed as far as possible from their pain but there are inherent problems with this.

Often with the use of opiate related drugs the increased dosages of these drugs administered result in the patient becoming drowsy and unresponsive. Increased dosages of these medicaments can also cause respiratory failure and in consequence may result in premature death.

Physicians and nurses are often reluctant to give large doses of analgesic drugs, even to dying patients. Their fear is that the large doses provided will lead to sedation or respiratory depression. The result of this can be that the patient's pain is not adequately catered for.

In a position statement on treatment of pain at the end of life, the American Pain Society has recognised that terminal illness can often be accompanied by pain that is so severe that death can seem preferable. It has also been recognised that a substantial proportion of patients, particularly those in minority groups, are receiving inadequate analgesic treatment (Cleeland et al., 1994).

The American Pain Society has recommended that pain is made more visible and is therefore routinely charted as the fifth vital sign.

The use of *cannabis* as a medicine has long been known and during the 19$^{th}$ Century preparations of *cannabis* were recommended as a hypnotic sedative which were useful for the treatment of hysteria, delirium, epilepsy, nervous insomnia, migraine, pain and dysmenorrhoea.

Until recent times the administration of *cannabis* to a patient could only be achieved by preparation of *cannabis* by decoction in ethanol, which could then be swallowed or by the patient inhaling the vapours of *cannabis* by smoking the dried plant material. Recent methods have sought to find new ways to deliver cannabinoids to a patient including those which bypass the stomach and the associated first pass effect of the liver which can remove up to 90% of the active ingested dose and avoid the patient having to inhale unhealthy tars and associated carcinogens into their lungs.

Such dosage forms include administering the cannabinoids to the sublingual or buccal mucosae, inhalation of a cannabinoid vapour by vaporisation or nebulisation, enemas or solid dosage forms such as gels, capsules, tablets, pastilles and lozenges.

In 1988 a study was undertaken in order to determine the analgesic and anti-inflammatory activity of various cannabinoids and cannabinoid pre-cursors. Oral administration of CBD was found to be the most effective at inhibition of PBQ-induced writhing in mice. THC and CBN were found to be least effective at reducing analgesia and inflammation (Formukong et al., 1988).

Holdcroft et al. have shown that cannabinoids can have analgesic and possible anti-inflammatory properties. Administration of 50 mg of THC to a patient with Mediterranean fever resulted in a highly significant reduction in the amount of analgesia that the patient required (Holdcroft et al., 1997a).

A follow-on publication by the same authors examined the oral administration of oil of *cannabis*. The capsules containing 5.75% THC, 4.73% CBD and 2.42% CBN were administered to a patient with familial Mediterranean fever. During the 3 weeks of active treatment there was a decrease in the amount of escape medication (morphine) required by the patient (Holdcroft et al., 1997b). There were no changes in the measured inflammatory markers.

The use of different ratios of cannabinoids such as THC or CBD or their propyl variants, tetrahydrocannabinovarin (THCV) and cannabidivarin (CBDV), in the treatment of different diseases and conditions has previously been described in co-owned UK patent application GB2377633.

Specific ratios of THC and CBD or THCV and CBDV were reported to have been useful in the treatment or management of specific diseases or medical conditions. The following table details some of these areas.

| Product Group Area | Ratio THC:CBD | Target Therapeutic |
| --- | --- | --- |
| High THC | >95:5 | Cancer pain; Migraine; Appetite stimulation. |
| Even ratio | 50:50 | Multiple sclerosis; Spinal cord injury; Peripheral neuropathy; Neurogenic pain. |
| Broad ratio CBD | <25:75 | Rheumatoid arthritis; inflammatory bowel disease. |
| High CBD | <5:95 | Psychotic disorders (schizophrenia); Epilepsy; Movement disorders; Stroke; Head injury; Disease modification in rheumatoid arthritis and other |

| Product Group Area | Ratio THC:CBD | Target Therapeutic |
|---|---|---|
| | | inflammatory conditions; Appetite suppression. |

A major disadvantage with the currently available drug therapies to treat severe chronic pain can be that the use of opioid based drugs may lead to unwanted side effects including constipation, sedation, pruritus, nausea and vomiting, respiratory depression, dysphoria and hallucinations and urinary retention.

SUMMARY OF THE INVENTION

The use of a high THC extract has long been postulated to be an effective treatment of pain, especially in the treatment of pain caused by cancer.

Surprisingly, the applicants have found that the use of a *cannabis* based medicine extract that contains approximately equal amounts of the cannabinoids delta-9-tetrahydrocannabinol (THC) and cannabidiol (CBD) is more efficacious in the treatment of cancer pain than a *cannabis* based medicinal extract containing THC alone.

The applicants have also found, unexpectedly, that some of the unwanted side effects caused by opiates such as constipation are relieved by treatment with the combination of the cannabinoids CBD and THC.

According to the first aspect of the present invention there is provided a method of treatment of cancer related pain comprising administering to a subject in need thereof a combination of the cannabinoids cannabidiol (CBD) and delta-9-tetrahydrocannabinol (THC), wherein the ratio of CBD:THC by weight is between 10:1 and 1:10.

Preferably the ratio of CBD:THC by weight is between 5:1 and 1:5. More preferably the ratio of CBD:THC by weight is between 2:1 and 1:2. More preferably the ratio of CBD:THC by weight is between about 1:0.9 and 0.9:1, still more preferably the ratio of CBD:THC by weight is about 1:1, and yet more preferably the ratio of CBD:THC by weight is 0.93:1.

Preferably the method comprises the treatment of cancer related pain which is caused by cancer of the breast; cancer of the prostate; cancer of the lung; cancer of the cervix; cancer of the rectum; cancer of the stomach; or cancer of the colon.

Preferably the dose of medicament to be administered to the subject suffering from cancer related pain is formulated such that a patient is able to titrate their dose. Examples of titratable dosage forms are gel, gel spray, liquid and vapor.

The term "titrate" is defined as meaning that the patient is provided with a medication that is in such a form that smaller doses than the unit dose can be taken.

A "unit dose" is herein defined as a maximum dose of medication that can be taken at any one time or within a specified dosage period such as 3 hours.

Titration of doses are beneficial to the patient as they are able to take smaller doses of the medication to achieve efficacy. It is understandable that not all patients will require exactly the same dose of medication, for example patients of a larger build or faster metabolism may require a higher dose than that required by a patient that is of a smaller build or slower metabolism. Different patients may also present with different degrees of complaints (e.g., cancer-related pain) and as such may require larger or smaller doses in order to treat the complaints (e.g., cancer-related pain) effectively. The benefits of such a dosage form over dosage forms such as tablets, where smaller doses are difficult to take, are therefore evident.

Unit dose ranges are preferably in the range of between 5 and 25 mg of each cannabinoid CBD and THC, more preferably in the range of 10 to 20 mg of each cannabinoid, more preferably in the range of 12 to 14 mg of each cannabinoid more preferably still in the range of 12.5 to 13.5 mg of each cannabinoid.

Preferably the maximum daily dosage dose of medicament to be administered to the subject suffering from cancer related pain is less than or equal to 120 mg CBD and less than or equal to 130 mg THC.

A combination of cannabinoids such as THC and CBD to a patient can be administered at the same time, for example wherein the cannabinoids are contained in the same formulation. The cannabinoids also can be administered at separate times. For example, a formulation containing CBD could be administered to a patient at a fixed time prior to a formulation containing THC in order to ameliorate some of the side effects of THC, which CBD is known to improve or vice versa. The two cannabinoids could also be administered consecutively to a patient if required.

A further embodiment of the invention provides a method of treatment of cancer related pain whereby a combination of the cannabinoids CBD and THC are packaged for delivery such that delivery is targeted to a specific area such as a sublingual area; a buccal area; an oral area; a rectal area; a nasal area; and/or via the pulmonary system. Preferably the cannabinoids are packaged for delivery sublingually or buccally, more preferably as a sublingual or buccal spray.

Preferably the cannabinoids are one of the following forms: gel; gel spray; tablet; liquid; capsule or a form for vaporisation.

Additionally the pharmaceutical formulation preferably further comprises one or more carrier solvents. Preferably the carrier solvents are ethanol and/or propylene glycol. More preferably the ratio of ethanol to propylene glycol is between 4:1 and 1:4. More preferably still the ratio is substantially 1:1.

Pharmaceutical formulations are prepared using methods and compositions known to those skilled in the art. Preferred components of suitable formulations are provided, for example, in US published applications US 2004/0034108, US 2003/0021752 and US 2002/0136752, and PCT published applications WO 2004/016246 and WO 02/064109.

Preferably the invention provides a combination of cannabinoids, which are present as one or more *cannabis* based medicine extracts (CBME). In one embodiment the CBME are produced by extraction with supercritical or subcritical $CO_2$. In an alternative embodiment the CBME are produced by extraction from plant material by volatilisation with a heated gas. Preferably the CBME contain all of the naturally occurring cannabinoids in the plant material. Alternatively synthetic or highly purified isolates of the cannabinoids can be used.

More preferably the method of treatment of cancer related pain comprises a combination of cannabinoids which are: a *cannabis* based medicinal extract which comprises THC at more than 90% of the total cannabinoid content in the extract; and a *cannabis* based medicinal extract which comprises CBD at more than 90% of the total cannabinoid content in the extract.

In a further embodiment of the invention the treatment of cancer related pain additionally comprises administration of the cannabinoids CBD and THC in an approximately equal amount by weight in combination with one or more opiate or opiate related drugs. An alternative embodiment of the invention comprises the administration of the cannabinoids CBD and THC in an approximately equal amount by weight in addition to one or more opiate or opiate related drugs.

The term "approximately equal" is used to refer to ratios of cannabinoids which are in the range of between 0.9:1 to 1:0.9 (THC:CBD). Additionally the term "1:1" is taken herein to refer to approximately equal amounts of cannabinoids.

Opiate or opiate related drugs include but are not limited to morphine, drugs chemically related to morphine and also non-related structures which act at the same receptors in the brain.

The term "in combination" refers to administration of the cannabinoids at the same time and in the same formulation as the opiate or opiate related drug.

The term "in addition to" refers to administration of the cannabinoids to patient who is already being administered opiate or opiate related drugs.

According to a second aspect of the present invention there is provided a method of treatment of constipation comprising administering to a subject in need thereof a combination of the cannabinoids cannabidiol (CBD) and delta-9-tetrahydrocannabinol (THC), wherein the ratio of CBD:THC by weight is between 10:1 and 1:10.

Preferably the constipation is associated with opiate or opiate related drug therapy.

The methods of constipation treatment include the cannabinoid compositions, dosage forms, modes of delivery, etc. as described above in relation to the methods of treatment of cancer related pain.

Certain aspects of this invention are further described, by way of example only, with reference to the accompanying drawings.

BRIEF DESCRIPTION OF THE DRAWINGS

FIG. 1 shows an HPLC chromatographic profile which characterises a CBD-containing *cannabis* based medicine extract.

FIG. 2 shows an HPLC chromatographic profile which characterises a THC-containing *cannabis* based medicine extract.

FIG. 3 shows an HPLC chromatographic profile which characterises a *cannabis* based medicine extract comprising substantially equal quantities of CBD and THC.

DETAILED DESCRIPTION OF THE INVENTION

A *cannabis* based medicine extract (CBME) was prepared as outlined in Example 1 and contained approximately equal amounts of the cannabinoids THC and CBD and this was administered to patients with cancer related pain.

A double blind, randomised, parallel group, placebo-controlled, comparative study of the efficacy, safety and tolerability of different *cannabis* based medicine extracts (CBME) was undertaken. The test articles that were studied were CBME THC:CBD (1:1) (THC 27 mg/ml), (CBD 25 mg/ml); CBME THC (THC 27 mg/ml); and matching placebo.

The study population were patients who were hospice or hospital in or outpatients, aged 18 years or above, who had terminal cancer and were experiencing pain that was not responding adequately to strong opiate or opiate related therapy.

The aim of the study was to determine whether the administration of either the combined THC and CBD or THC alone could be used to relieve pain in patients with cancer related pain.

The primary outcome of the study was to compare each CBME versus the placebo in the change from baseline in the patient's pain score at visit 3. The use of escape analgesia was also measured as a co-primary end-point of the study.

The secondary objectives of the study were to the use of regular maintenance medication, the dose of study medication and also whether there was a change from baseline in sleep disturbance, nausea, memory, appetite, concentration, Brief Pain Inventory (BPI) scores and quality of life compared to placebo.

Unexpectedly the *cannabis* based medicine extract containing approximately equal quantities of THC and CBD produced a greater degree of pain relief than the CBME that contained THC alone.

Additionally patients that were administered the CBME containing approximately equal amounts of THC and CBD reported in their quality of life questionnaire a lesser degree of constipation in comparison to their baseline scores at the beginning of the trial.

The features of the invention are illustrated further by reference to the following examples:

Example 1

Preparation of *Cannabis* Based Medicine Extracts (CBME)

Medicinal *cannabis* was produced and prepared with reference to the method disclosed in WO 02/064109 (Example 15). The resulting plant material was processed as described in the flow chart below. The process of manufacture of a High THC or High CBD *cannabis* based medicine extract is described.

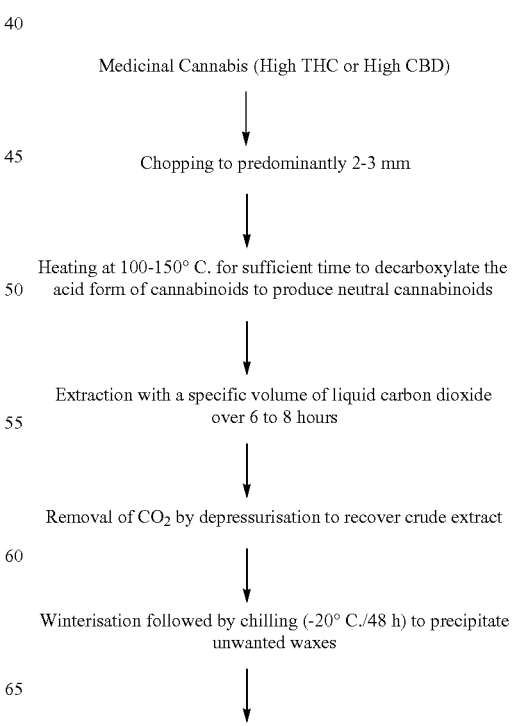

Medicinal Cannabis (High THC or High CBD)

↓

Chopping to predominantly 2-3 mm

↓

Heating at 100-150° C. for sufficient time to decarboxylate the acid form of cannabinoids to produce neutral cannabinoids

↓

Extraction with a specific volume of liquid carbon dioxide over 6 to 8 hours

↓

Removal of $CO_2$ by depressurisation to recover crude extract

↓

Winterisation followed by chilling (-20° C./48 h) to precipitate unwanted waxes

↓

-continued

Removal of unwanted waxy material by cold filtration

↓

Removal of ethanol from the filtrate by thin film evaporation under reduced pressure The resulting extract is referred to as a *cannabis* based medicinal drug extract and is also classified as a Botanical Drug Substance according to the US Food and Drug Administration Guidance for Industry Botanical Drug Products.

The quantity of cannabinoid in the CBME can be accurately assessed by way of measurement by HPLC with reference to the method disclosed in WO 02/064109 (Example 16).

An example of an HPLC chromatogram of a CBD-containing CBME produced using a high CBD medicinal *cannabis* plant extracted with $CO_2$ is shown in FIG. 1. An example of an HPLC chromatogram of a THC-containing CBME produced using a high THC medicinal *cannabis* plant extracted with $CO_2$ is shown in FIG. 2. An example of an HPLC chromatogram containing the relevant ratios of THC and CBD CBMEs is shown in FIG. 3.

Example 2

Assessment and Comparison of the Efficacy, Safety and Tolerabilty of *Cannabis* Based Medicine Extracts by Way of a Clinical Trial in Human Patients with Cancer Related Pain A multi-centre, double blind, randomised, parallel group, placebo controlled, comparative study was undertaken in order to evaluate the efficacy, safety and tolerability of *cannabis* based medicine extracts (CBME) in patients with cancer related pain. The *cannabis* based medicine extracts contained either delta-9-tetrahydrocannabinol (THC) at a concentration of 27 mg/ml and cannabidiol (CBD) at a concentration of 25 mg/ml in ethanol:propylene glycol (50:50) excipient or delta-9-tetrahydrocannabinol (THC) at a concentration of 27 mg/ml in ethanol:propylene glycol (50:50) excipient. The CBME was presented in a pump action spray where each activation delivers 100 µl of spray, containing THC (2.7 mg) and CBD (2.5 mg).

The subjects in the study were randomised equally to either one of the *cannabis* based medicine extracts or placebo. The placebo matched the appearance, smell and taste of the active formulation, but containing no active components. The excipient was ethanol:propylene glycol (50:50). Again the placebo was presented in a pump action spray where each activation delivers 100 µl of spray.

Patient Diary Cards were required to be completed daily throughout the study. The patient could take strong opioid escape medication at any time throughout the study although other analgesic medications were required to be kept constant.

The maximum dose of study medication that was allowed to be taken was 8 sprays at any one time or within any 3 hour interval, with a maximum of 48 sprays within any 24 hour interval.

Patients were randomised to receive either THC:CBD (1:1), THC or placebo. The randomisation was in the ratio of 1:1:1 (THC:CBD (1:1), THC, Placebo).

It should be noted that the terms 1:1 THC:CBD or equal amounts of THC:CBD refer to approximately equal.

At the screening visit the patients were assessed for compliance with the inclusion or exclusion criteria and advised of the study requirements. Once the patient had provided informed consent, eligible patients were asked to complete run-in diaries for a period of 2 days before returning for visit 1.

At visit 1 the patient's previous medical history was taken along with assessment by two questionnaires. These were the Brief Pain Inventory Short Form (BPI-SF) questionnaire and the European Organisation for Research and Treatment of Cancer (EORTC) Quality of Life questionnaire (QLQ-C30).

Patients whose level of pain was equal to or greater than 4 on a BS-11 pain score on at least one occasion per day during the 2 day run-in period and who fulfilled the study entry criteria and who were willing to continue were allocated a study number and dosing with study medication was commenced.

Patients were provided with a diary and instructed how to fill it in. Assessments were to be made on a daily basis.

Patients were allowed to adjust their dose of study medication to achieve optimal pain control based on pain scores, adverse event profiles and escape medication usage.

At visit 2, approximately 7 to 10 days after visit 1 a review of the patient's clinical status was undertaken which included pain control, adverse event profile, strong opioid escape medication usage, change in concomitant medication and change in strong opioid medication.

At visit 3, which took place approximately 14 to 20 days after visit 1, the patient's clinical status was again reviewed as detailed at visit 2. The patients were also asked to complete the BPI-SF and QLQ-C30 questionnaires.

The Box Scale (BS-11) pain score where 0 equals "no pain" and 10 equals "very bad pain" were used as a primary measure of efficacy of the study medication for pain intensity.

The patient diary asked patients to record BS-11 scores for pain three times per day at morning (on waking), lunchtime and evening (just prior to going to bed).

BS-11 scores referring to the previous 24 hours were recorded daily in the evening for sleep, nausea, memory, concentration and appetite.

The number of sprays of study medication and the time it was taken, the doses of regular maintenance medication that was taken and the dose and time of any escape medication taken was also recorded in the diary.

Results:

Some of the data collated from this study is described below.

Comparison of Mean Numeric Rating Score (NRS) Pain Scores at All Assessment Periods in Patients with Cancer Related Pain when Administered a *Cannabis* Based Medicine Extract Containing an Approximately Equal Ratio of THC (27 mg/ml) and CBD (25 mg/ml) or THC (27 mg/ml) in Intention to Treat (ITT) Population.

The efficacy, safety and tolerability of two *cannabis* based medicine extracts were assessed as described above and the degree of pain at different times of the day was recorded by self assessment on a daily basis. The data was collated and statistical analysis was undertaken. Patients assessed pain on a scale of 0 (no pain) to 10 (extremely bad pain). Table 1 illustrates the mean 11-point NRS pain scores at all assessment periods in the intention to treat (ITT) population.

TABLE 1

|  |  | THC:CBD (27 mg/ml:25 mg/ml) (N = 59) | THC (27 mg/ml) (N = 58) | Placebo (N = 58) |
|---|---|---|---|---|
| Baseline | Mean | 5.68 | 5.77 | 6.05 |
|  | Std Dev | 1.24 | 1.33 | 1.32 |
|  | Median | 5.67 | 5.67 | 5.70 |
|  | Minimum | 2.33 | 2.87 | 3.50 |
|  | Maximum | 8.25 | 9.33 | 9.56 |
| Week 1 | Mean | 4.90 | 5.01 | 5.52 |
|  | Std Dev | 1.52 | 1.72 | 1.77 |
|  | Median | 5.06 | 4.98 | 5.40 |
|  | Minimum | 0.91 | 1.62 | 1.17 |
|  | Maximum | 7.78 | 8.33 | 9.28 |
| Week 1 - change from baseline | Mean | −0.75 | −0.73 | −0.60 |
|  | Std Dev | 1.37 | 1.10 | 1.27 |
|  | Median | −0.72 | −0.62 | −0.49 |
|  | Minimum | −5.36 | −3.33 | −4.22 |
|  | Maximum | 3.47 | 2.33 | 3.78 |
| Week 2 | Mean | 4.38 | 4.98 | 5.10 |
|  | Std Dev | 1.69 | 1.70 | 1.63 |
|  | Median | 4.21 | 4.92 | 5.04 |
|  | Minimum | 0.14 | 1.83 | 1.00 |
|  | Maximum | 8.10 | 8.17 | 8.24 |
| Week 2 - change from baseline | Mean | −1.31 | −0.94 | −0.89 |
|  | Std Dev | 1.57 | 1.10 | 1.47 |
|  | Median | −1.26 | −0.86 | −0.90 |
|  | Minimum | −6.12 | −3.77 | −4.60 |
|  | Maximum | 1.76 | 1.50 | 2.74 |
| Last 3 days | Mean | 4.34 | 4.82 | 5.39 |
|  | Std Dev | 1.76 | 1.77 | 1.85 |
|  | Median | 4.33 | 4.89 | 5.44 |
|  | Minimum | 0.00 | 1.67 | 0.78 |
|  | Maximum | 8.22 | 8.17 | 9.39 |
| Last 3 days - change from baseline | Mean | −1.32 | −0.93 | −0.73 |
|  | Std Dev | 1.64 | 1.15 | 1.51 |
|  | Median | −1.36 | −1.00 | −0.60 |
|  | Minimum | −6.89 | −3.94 | −4.82 |
|  | Maximum | 1.89 | 1.50 | 3.50 |

The baseline is a mean of all days in the run-in period and the last 3 days is a mean of last three days on study medication.

Statistical analysis of this data is shown in Tables 2 and 3.

Table 2 details the Analysis of Covariance of the mean 11-point NRS pain scores in the intention to treat (ITT) population.

TABLE 2

|  | Mean | Difference from placebo | 95% CI | p-value |
|---|---|---|---|---|
| THC:CBD (27 mg/ml:25 mg/ml) | −1.37 | −0.67 | [−1.21, −0.14] | 0.0142 |
| THC (27 mg/ml) | −1.01 | −0.32 | [−0.86, 0.22] | 0.2447 |
| Placebo | −0.69 | — | — | — |

Table 3 details the Non-Parametric Analysis of the mean 11-point NRS pain scores in the intention to treat (ITT) population.

TABLE 3

|  | Mean | Difference from placebo | 95% CI | p-value |
|---|---|---|---|---|
| THC:CBD (27 mg/ml:25 mg/ml) | −1.36 | −0.55 | [−1.08, 0.00] | 0.0592 |
| THC (27 mg/ml) | −1.00 | −0.24 | [−0.76, 0.28] | 0.3552 |
| Placebo | −0.60 | — | — | — |

The data displayed in the above two tables is for the change in baseline, which is the final result minus baseline scores. A value less than zero indicates a decrease in pain score from baseline. A difference from placebo of less than zero indicates a greater decrease from baseline in active treatment group compared with placebo.

Tables 4 and 5 summarise the NRS for pain by responders in the ITT population. Table 4 details the actual number of responders who had a reduction in pain score from baseline levels.

TABLE 4

|  |  | THC:CBD (27 mg/ml:25 mg/ml) (N = 60) (%) | THC (27 mg/ml) (N = 58) (%) | Placebo (N = 59) (%) |
|---|---|---|---|---|
| Reduction | >0 | 41 (68%) | 41 (71%) | 39 (66%) |
|  | ≥10% | 33 (55%) | 33 (57%) | 27 (46%) |
|  | ≥20% | 30 (50%) | 21 (36%) | 21 (36%) |
|  | ≥30% | 23 (38%) | 12 (21%) | 12 (20%) |
|  | ≥40% | 12 (20%) | 10 (17%) | 6 (10%) |
|  | ≥50% | 6 (10%) | 3 (5%) | 4 (7%) |

TABLE 5

|  |  | OR (95% C.I.) THC:CBD (27 mg/ml:25 mg/ml) vs. Placebo | OR (95% C.I.) THC (27 mg/ml) vs. Placebo |
|---|---|---|---|
| Reduction | >0 | 1.49 (0.63, 3.52) | 1.62 (0.68, 3.90) |
|  | ≥10% | 1.77 (0.83, 3.80) | 1.87 (0.86, 4.03) |
|  | ≥20% | 2.17 (1.01, 4.68) | 1.13 (0.52, 2.45) |
|  | ≥30% | 2.81 (1.22, 6.50) | 1.10 (0.44, 2.73) |
|  | ≥40% | 2.44 (0.84, 7.06) | 1.98 (0.67, 5.91) |
|  | ≥50% | 1.66 (0.44, 6.25) | 0.80 (0.17, 3.74) |

The Odds Ratio (OR) compares whether the probability of an event is the same for two groups. An OR which is equal to 1 infers that the event is equally likely to occur in both groups. An OR which is greater than 1 implies the event is more likely to occur in the first group and an OR less than 1 implies that the event is less likely to occur in the first group.

The data shown above illustrates that the study medication which contained approximately equal amounts of THC and CBD resulted in a greater change from the baseline in pain scores when compared to the study medication which contained THC alone. As such the statistical analysis data demonstrates that the 1:1 THC:CBD is shown statistically to be more efficacious than the THC alone.

The data demonstrates that there is a higher degree of responders who experienced a greater than or equal to 30% reduction in pain in the 1:1 THC:CBD group than in the THC alone group.

Comparison of Mean Numeric Rating Score (NRS) Pain Scores at All Assessment Periods in Patients with Cancer Related Pain when Administered a *Cannabis* Based Medicine Extract Containing an Approximately Equal Ratio of THC (27 mg/ml) and CBD (25 mg/ml) or THC (27 mg/ml) in Per-Protocol Population.

The efficacy, safety and tolerability of two *cannabis* based medicine extracts were assessed as described above and the degree of pain at different times of the day was recorded by self assessment on a daily basis. The data was collated and statistical analysis was undertaken. Patients assessed pain on a scale of 0 (no pain) to 10 (extremely bad pain). Table 6 illustrates the mean 11-point NRS pain scores at all assessment periods in the per-protocol population.

TABLE 6

|  |  | THC:CBD (27 mg/ml:25 mg/ml) (N = 43) | THC (27 mg/ml) (N = 47) | Placebo (N = 47) |
|---|---|---|---|---|
| Baseline | Mean | 5.62 | 5.71 | 5.92 |
|  | Std Dev | 1.25 | 1.40 | 1.34 |
|  | Median | 5.67 | 5.67 | 5.58 |
|  | Minimum | 2.33 | 2.87 | 3.50 |
|  | Maximum | 8.25 | 9.33 | 9.56 |
| Week 1 | Mean | 4.78 | 4.92 | 5.31 |
|  | Std Dev | 1.54 | 1.63 | 1.84 |
|  | Median | 4.89 | 4.79 | 5.22 |
|  | Minimum | 0.91 | 2.24 | 1.17 |
|  | Maximum | 7.78 | 8.33 | 9.28 |
| Week 1 - change from baseline | Mean | −0.81 | −0.79 | −0.61 |
|  | Std Dev | 1.43 | 1.05 | 1.34 |
|  | Median | −0.67 | −0.63 | −0.53 |
|  | Minimum | −5.36 | −3.33 | −4.22 |
|  | Maximum | 3.47 | 2.33 | 3.78 |
| Week 2 | Mean | 4.32 | 4.88 | 5.01 |
|  | Std Dev | 1.66 | 1.71 | 1.66 |
|  | Median | 4.07 | 4.81 | 4.94 |
|  | Minimum | 0.14 | 1.83 | 1.00 |
|  | Maximum | 8.10 | 8.17 | 8.24 |
| Week 2 - change from baseline | Mean | −1.33 | −0.98 | −0.80 |
|  | Std Dev | 1.47 | 1.11 | 1.48 |
|  | Median | −1.39 | −0.86 | −0.81 |
|  | Minimum | −6.12 | −3.77 | −4.60 |
|  | Maximum | 1.76 | 1.50 | 2.74 |
| Last 3 days | Mean | 4.20 | 4.79 | 5.27 |
|  | Std Dev | 1.64 | 1.73 | 1.90 |
|  | Median | 4.00 | 4.89 | 5.44 |
|  | Minimum | 0.00 | 1.78 | 0.78 |
|  | Maximum | 8.22 | 8.17 | 9.39 |
| Last 3 days - change from baseline | Mean | −1.42 | −0.92 | −0.65 |
|  | Std Dev | 1.43 | 1.15 | 1.53 |
|  | Median | −1.44 | −1.00 | −0.56 |
|  | Minimum | −6.27 | −3.94 | −4.82 |
|  | Maximum | 1.89 | 1.50 | 3.50 |

The baseline is a mean of all days in the run-in period and the last 3 days is a mean of last three days on study medication.

Statistical analysis of this data is shown in Tables 7 and 8.

Table 7 details the Analysis of Covariance of the mean 11-point NRS pain scores in the per-protocol population.

TABLE 7

|  | Mean | Difference from placebo | 95% CI | p-value |
|---|---|---|---|---|
| THC:CBD (27 mg/ml:25 mg/ml) | −1.41 | −0.81 | [−1.37, −0.25] | 0.0047 |
| THC (27 mg/ml) | −0.94 | −0.35 | [−0.89, 0.20] | 0.2085 |
| Placebo | −0.59 | — | — | — |

Table 8 details the Non-Parametric Analysis of the mean 11-point NRS pain scores in the per-protocol population.

TABLE 8

|  | Mean | Difference from placebo | 95% CI | p-value |
|---|---|---|---|---|
| THC:CBD (27 mg/ml:25 mg/ml) | −1.44 | −0.78 | [−1.38, −0.19] | 0.0120 |
| THC (27 mg/ml) | −1.00 | −0.28 | [−0.83, 0.25] | 0.2959 |
| Placebo | −0.56 | — | — | — |

The data displayed in the above two tables is for the change in baseline, which is the final result minus baseline scores. A value less than zero indicates a decrease in pain score from baseline. A difference from placebo of less than zero indicates a greater decrease from baseline in active treatment group compared with placebo.

Tables 9 and 10 summarise the NRS for pain by responders in the per-protocol population. Table 9 details the actual number of responders who had a reduction in pain score from baseline levels.

TABLE 9

|  |  | THC:CBD (27 mg/ml:25 mg/ml) (N = 43) (%) | THC (27 mg/ml) (N = 47) (%) | Placebo (N = 47) (%) |
|---|---|---|---|---|
| Reduction | >0 | 36 (84%) | 38 (81%) | 32 (68%) |
|  | ≥10% | 30 (70%) | 30 (64%) | 23 (49%) |
|  | ≥20% | 27 (63%) | 18 (38%) | 17 (36%) |
|  | ≥30% | 20 (47%) | 11 (23%) | 8 (17%) |
|  | ≥40% | 10 (23%) | 9 (19%) | 5 (11%) |
|  | ≥50% | 5 (12%) | 2 (4%) | 4 (9%) |

TABLE 10

|  |  | OR (95% C.I.) THC:CBD (27 mg/ml:25 mg/ml) vs. Placebo | OR (95% C.I.) THC (27 mg/ml) vs. Placebo |
|---|---|---|---|
| Reduction | >0 | 2.41 (0.87, 6.66) | 1.98 (0.76, 5.12) |
|  | ≥10% | 2.41 (1.01, 5.73) | 1.84 (0.81, 4.20) |
|  | ≥20% | 2.98 (1.26, 7.02) | 1.10 (0.47, 2.53) |
|  | ≥30% | 4.24 (1.61, 11.2) | 1.49 (0.54, 4.12) |
|  | ≥40% | 2.55 (0.79, 8.17) | 1.99 (0.61, 6.46) |
|  | ≥50% | 1.41 (0.35, 5.65) | 0.48 (0.08, 2.74) |

The Odds Ratio (OR) compares whether the probability of an event is the same for two groups. An OR which is equal to 1 infers that the event is equally likely to occur in both groups. An OR which is greater than 1 implies the event is more likely to occur in the first group and an OR less than 1 implies that the event is less likely to occur in the first group.

The data shown above illustrates that the study medication which contained approximately equal amounts of THC and CBD resulted in a greater change from the baseline in pain scores when compared to the study medication which contained THC alone. As such the statistical analysis data demonstrates that the 1:1 THC:CBD is shown statistically to be more efficacious than the THC alone.

The data demonstrates that there is a higher degree of responders who experienced a greater than or equal to 30% reduction in pain in the 1:1 THC:CBD group than in the THC alone group.

Because this data from the per-protocol population shows the same as the intention to treat population it means that the overall data set is robust.

Comparison of Use of Escape Medication in Patients with Cancer Related Pain when Administered a *Cannabis* Based Medicine Extract Containing an Approximately Equal Ratio of THC (27 mg/ml) and CBD (25 mg/ml) or THC (27 mg/ml) in Intention to Treat (ITT) Population.

The efficacy, safety and tolerability of two *cannabis* based medicine extracts were assessed as described above and the number of days in which escape medication was used was recorded. The data was collated and statistical analysis was undertaken. Table 11 illustrates the mean doses per day and its change from baseline in the intention to treat (ITT) population.

TABLE 11

|  |  | THC:CBD (27 mg/ml:25 mg/ml) (N = 60) (%) | THC (27 mg/ml) (N = 58) (%) | Placebo (N = 59) (%) |
|---|---|---|---|---|
| No of days used | N | 54 | 52 | 57 |
|  | 0 | 22 (37%) | 18 (31%) | 21 (36%) |
|  | 1 | 3 (5%) | 1 (2%) | 6 (10%) |
|  | 2 | 3 (5%) | 5 (9%) | 3 (5%) |
|  | 3 | 26 (43%) | 28 (48%) | 27 (46%) |
| Baseline | N | 53 | 52 | 56 |
|  | Mean | 0.91 | 1.10 | 0.80 |
|  | Std Dev | 0.906 | 1.048 | 0.892 |
|  | Median | 1.00 | 1.00 | 0.71 |
|  | Min, Max | 0.00, 3.50 | 0.00, 5.00 | 0.00, 4.00 |
| Last 3 days | N | 54 | 52 | 57 |
|  | Mean | 0.72 | 0.88 | 0.68 |
|  | Std Dev | 0.821 | 0.852 | 0.662 |
|  | Median | 0.67 | 1.00 | 0.67 |
|  | Min, Max | 0.00, 4.00 | 0.00, 4.33 | 0.00, 2.00 |
| Change from baseline | N | 53 | 52 | 56 |
|  | Mean | −0.17 | −0.23 | −0.13 |
|  | Std Dev | 0.500 | 0.743 | 0.730 |
|  | Median | 0.00 | 0.00 | 0.00 |
|  | Min, Max | −1.50, 1.00 | −3.00, 2.00 | −2.67, 1.33 |

The baseline is a mean of all days in the run-in period and the last 3 days is a mean of last three days on study medication.

Statistical analysis of this data is shown in Tables 12 to 15.

Table 12 details the analysis of number of days that escape medication was used in the intention to treat (ITT) population.

TABLE 12

|  | N | OR for increasing No of days | 95% CI | p-value |
|---|---|---|---|---|
| THC:CBD (27 mg/ml:25 mg/ml) | 60 | 0.96 | [0.46, 2.02] | 0.6973 |
| THC (27 mg/ml) | 58 | 1.20 | [0.57, 2.54] | 0.5545 |
| Placebo | 59 | — | — | — |

Table 13 details the analysis of number of days that escape medication used in the intention to treat (ITT) population when adjusted for baseline proportion of days.

TABLE 13

|  | N | OR for increasing No of days | 95% CI | p-value |
|---|---|---|---|---|
| THC:CBD (27 mg/ml:25 mg/ml) | 60 | 0.75 | [0.29, 1.89] | 0.9165 |
| THC (27 mg/ml) | 58 | 0.61 | [0.23, 1.57] | 0.4143 |
| Placebo | 59 | — | — | — |

Table 14 details analysis of covariance of the mean number of doses of escape medication used per day and the change from baseline in the intention to treat (ITT) population.

TABLE 14

|  | Mean | Difference from placebo | 95% CI | p-value |
|---|---|---|---|---|
| THC:CBD (27 mg/ml:25 mg/ml) (N = 53) | −0.19 | −0.04 | [−0.25, 0.16] | 0.6877 |
| THC (27 mg/ml) (N = 52) | −0.14 | 0.01 | [−0.19, 0.22] | 0.8992 |
| Placebo (N = 56) | −0.15 | — | — | — |

Table 15 details the Non-Parametric Analysis of the mean number of doses of escape medication used per day and change from baseline in the ITT population.

TABLE 15

|  | Mean | Difference from placebo | 95% CI | p-value |
|---|---|---|---|---|
| THC:CBD (27 mg/ml:25 mg/ml) (N = 53) | 0.00 | 0.00 | [−0.08, 0.00] | 0.4223 |
| THC (27 mg/ml) (N = 52) | 0.00 | 0.00 | [−0.25, 0.00] | 0.2552 |
| Placebo (N = 56) | 0.00 | — | — | — |

The data displayed in the above two tables is for the change in baseline, which is the final result minus baseline scores. A value less than zero indicates a decrease in pain score from baseline. A difference from placebo of less than zero indicates a greater decrease from baseline in active treatment group compared with placebo.

The data for the use of escape medication in patients with cancer related pain in the intention to treat population shows that patients were equally as likely to use escape medication whether they were taking study medication containing approximately equal amount of THC and CBD or THC alone as they would be if they were taking the placebo.

This data is important as it shows that there was no cumulative effect of the cannabinoids upon the opioid medication that the patients were already taking. This would enable doctors and health care workers therefore to still allow patients the use of their escape medication to treat breakthrough pain. Comparison of Use of Escape Medication in Patients with Cancer Related Pain when Administered a *Cannabis* Based Medicine Extract Containing an Approximately Equal Ratio of THC (27 mg/ml) and CBD (25 mg/ml) or THC (27 mg/ml) in Per-Protocol Protocol Population.

The efficacy, safety and tolerability of two *cannabis* based medicine extracts were assessed as described above and the number of days in which escape medication was used was recorded. The data was collated and statistical analysis was undertaken. Table 16 illustrates the mean doses per day and its change from baseline in the per-protocol population.

TABLE 16

|  |  | THC:CBD (27 mg/ml:25 mg/ml) (N = 60) (%) | THC (27 mg/ml) (N = 58) (%) | Placebo (N = 59) (%) |
|---|---|---|---|---|
| No of days used | N | 54 | 52 | 57 |
|  | 0 | 22 (37%) | 18 (31%) | 21 (36%) |
|  | 1 | 3 (5%) | 1 (2%) | 6 (10%) |
|  | 2 | 3 (5%) | 5 (9%) | 3 (5%) |
|  | 3 | 26 (43%) | 28 (48%) | 27 (46%) |
| Baseline | N | 53 | 52 | 56 |
|  | Mean | 0.91 | 1.10 | 0.80 |
|  | Std Dev | 0.906 | 1.048 | 0.892 |

TABLE 16-continued

|  |  | THC:CBD (27 mg/ml:25 mg/ml) (N = 60) (%) | THC (27 mg/ml) (N = 58) (%) | Placebo (N = 59) (%) |
|---|---|---|---|---|
|  | Median | 1.00 | 1.00 | 0.71 |
|  | Min, Max | 0.00, 3.50 | 0.00, 5.00 | 0.00, 4.00 |
| Last 3 | N | 54 | 52 | 57 |
| days | Mean | 0.72 | 0.88 | 0.68 |
|  | Std Dev | 0.821 | 0.852 | 0.662 |
|  | Median | 0.67 | 1.00 | 0.67 |
|  | Min, Max | 0.00, 4.00 | 0.00, 4.33 | 0.00, 2.00 |
| Change | N | 53 | 52 | 56 |
| from | Mean | −0.17 | −0.23 | −0.13 |
| baseline | Std Dev | 0.500 | 0.743 | 0.730 |
|  | Median | 0.00 | 0.00 | 0.00 |
|  | Min, Max | −1.50, 1.00 | −3.00, 2.00 | −2.67, 1.33 |

The baseline is a mean of all days in the run-in period and the last 3 days is a mean of last three days on study medication.

Statistical analysis of this data is shown in Tables 17 to 20.

Table 17 details the analysis of number of days that escape medication used in the per-protocol population.

TABLE 17

|  | N | OR for increasing No of days | 95% CI | p-value |
|---|---|---|---|---|
| THC:CBD (27 mg/ml:25 mg/ml) | 43 | 0.99 | [0.43, 2.26] | 0.5338 |
| THC (27 mg/ml) | 47 | 1.55 | [0.69, 3.55] | 0.2253 |
| Placebo | 47 | — | — | — |

Table 18 details the analysis of number of days that escape medication used in the per-protocol population when adjusted for baseline proportion of days.

TABLE 18

|  | N | OR for increasing No of days | 95% CI | p-value |
|---|---|---|---|---|
| THC:CBD (27 mg/ml:25 mg/ml) | 43 | 0.47 | [0.14, 1.44] | 0.4273 |
| THC (27 mg/ml) | 47 | 0.48 | [0.14, 1.52] | 0.4863 |
| Placebo | 47 | — | — | — |

Table 19 details analysis of covariance of the mean number of doses of escape medication used per day and the change from baseline in the per-protocol population.

TABLE 19

|  | Mean | Difference from placebo | 95% CI | p-value |
|---|---|---|---|---|
| THC:CBD (27 mg/ml:25 mg/ml) (N = 43) | −0.17 | −0.09 | [−0.30, 0.12] | 0.4061 |
| THC (27 mg/ml) (N = 47) | −0.10 | −0.02 | [−0.22, 0.19] | 0.8774 |
| Placebo (N = 47) | −0.08 | — | — | — |

Table 20 details the Non-Parametric Analysis of the mean number of doses of escape medication used per day and change from baseline in the per-protocol population.

TABLE 20

|  | Mean | Difference from placebo | 95% CI | p-value |
|---|---|---|---|---|
| THC:CBD (27 mg/ml:25 mg/ml) (N = 43) | 0.00 | 0.00 | [−0.17, 0.00] | 0.1986 |
| THC (27 mg/ml) (N = 47) | 0.00 | 0.00 | [−0.25, 0.00] | 0.1038 |
| Placebo (N = 47) | 0.00 | — | — | — |

The data displayed in the above two tables is for the change in baseline, which is the final result minus baseline scores. A value less than zero indicates a decrease in pain score from baseline. A difference from placebo of less than zero indicates a greater decrease from baseline in active treatment group compared with placebo.

Again the data for the per-protocol population correlates with the intention to treat population.

Summary of EORTC QLQ-C30 Constipation Scale in Patients with Cancer Related Pain when Administered a *Cannabis* Based Medicine Extract Containing an Approximately Equal Ratio of THC (27 mg/ml) and CBD (25 mg/ml) or THC (27 mg/ml) in Intention to Treat (ITT) Population.

The efficacy, safety and tolerability of two *cannabis* based medicine extracts were assessed as described above and the degree of constipation as assessed by the EORTC QLQ-C30 constipation scale both at baseline during assessment in week 1 and at the end of the study. The data was collated and statistical analysis was undertaken. Table 21 illustrates the observed data and the change from baseline in the intention to treat (ITT) population.

TABLE 21

|  |  | THC:CBD (27 mg/ml:25 mg/ml) (N = 58) | THC (27 mg/ml) (N = 57) | Placebo (N = 59) |
|---|---|---|---|---|
| Baseline | Mean | 50.00 | 33.33 | 40.68 |
|  | Std Dev | 33.19 | 33.92 | 35.59 |
|  | Median | 33.33 | 33.33 | 33.33 |
|  | Minimum | 0.00 | 0.00 | 0.00 |
|  | Maximum | 100.00 | 100.00 | 100.00 |
| End of | Mean | 41.50 | 32.67 | 42.31 |
| Study | Std Dev | 31.57 | 28.96 | 35.00 |
|  | Median | 33.33 | 33.33 | 33.33 |
|  | Minimum | 0.00 | 0.00 | 0.00 |
|  | Maximum | 100.00 | 100.00 | 100.00 |
| Change | Mean | −8.16 | 0.68 | 3.21 |
| from | Std Dev | 24.09 | 24.99 | 25.79 |
| baseline | Median | 0.00 | 0.00 | 0.00 |
|  | Minimum | −100.0 | −66.67 | −66.67 |
|  | Maximum | 33.33 | 66.67 | 100.00 |

The baseline was taken at week 1.

Statistical analysis of this data is shown in Tables 22.

Table 22 details the Analysis of Covariance of the degree of constipation as assessed by the EORTC QLQ-C30 constipation scale in the intention to treat (ITT) population.

TABLE 22

|  | Adjusted Mean | Difference from placebo | 95% CI | p-value |
|---|---|---|---|---|
| THC:CBD (27 mg/ml:25 mg/ml) | −5.74 | −7.97 | [−16.81, 0.87] | 0.0769 |

TABLE 22-continued

| | Adjusted Mean | Difference from placebo | 95% CI | p-value |
|---|---|---|---|---|
| THC (27 mg/ml) | −3.11 | −5.35 | [−14.16, 3.47] | 0.2326 |
| Placebo | 2.23 | — | — | — |

The study described above was a Phase III trial and overall the study medication which contained approximately equal amounts of THC and CBD achieved a statistically significant improvement in comparison to placebo in pain as measured on a Numerical Rating Scale (p=0.014), this was a primary endpoint of the study. A responder analysis showed that approximately 40% of patients taking the study medication with approximately equal amounts of THC and CBD showed a greater than 30% improvement in their pain (p=0.024).

The study medication that contained THC alone did not show a significant effect in pain (p=0.24). The trial therefore suggests that the study medication that contains CBD along with THC is more effective at reducing cancer related pain than the study medication that contained THC alone.

The analysis of the second primary endpoint showed that there were no significant changes in the use of escape medication in either of the study medications as compared with placebo. The improvements in pain were therefore attributable to the positive effects of the study medication containing approximately equal amounts of THC and CBD.

The data also additionally shows that patients receiving the CBME containing approximately equal amounts of THC and CBD experienced a beneficial relief from opiate induced constipation.

It can therefore be concluded that a medication that contains approximately equal amounts of THC and CBD offers a new treatment option in the treatment of pain in patients with cancer related pain, and for treatment of constipation.

REFERENCES

Cleeland C. S., et al. (1994) Quality improvement guidelines for the treatment of acute pain and cancer pain. *Journal of the American Medical Association* 274, 1874-80

Formukong E. A., Evans A. T. and Evans F. J. (1988) Analgesic and Anti-inflammatory activity of constituents of *Cannabis sativa L. Inflammation* 12(4), 361-371

Holdcroft A. et al. (1997a) Pain relief with oral cannabinoids in familial Mediterranean fever. *Anaesthesia* 52(5), 483-6

Holdcroft A. et al. (1997b) Clinical trial experience with cannabinoids. *Pharm. Sci.* 3, 546-550

Those skilled in the art will recognize, or be able to ascertain using no more than routine experimentation, many equivalents to the specific embodiments of the invention described herein. Such equivalents are intended to be encompassed by the following claims.

All references disclosed herein are incorporated by reference in their entirety.

What is claimed is:

1. A method of treatment of constipation comprising administering to a subject in need thereof a combination of the cannabinoids cannabidiol (CBD) and delta-9-tetrahydrocannabinol (THC), wherein the ratio of CBD:THC by weight is between 10:1 and 1:10, wherein the constipation is associated with opiate or opiate related drug therapy.

* * * * *